(12) United States Patent
Barrios et al.

(10) Patent No.: US 9,045,507 B2
(45) Date of Patent: Jun. 2, 2015

(54) COUMARIN-BASED AMINO ACIDS FOR USE IN ENZYME ACTIVITY AND SUBSTRATE SPECIFICITY ASSAYS

(75) Inventors: Amy M. Barrios, Pasadena, CA (US); Sayantan Mitra, Los Angeles, CA (US)

(73) Assignee: UNIVERSITY OF SOUTHERN CALIFORNIA, Los Angeles, CA (US)

( * ) Notice: Subject to any disclaimer, the term of this patent is extended or adjusted under 35 U.S.C. 154(b) by 778 days.

(21) Appl. No.: 11/495,955

(22) Filed: Jul. 27, 2006

(65) Prior Publication Data
US 2007/0031892 A1 Feb. 8, 2007

Related U.S. Application Data

(60) Provisional application No. 60/703,942, filed on Jul. 27, 2005.

(51) Int. Cl.
| | |
|---|---|
| G01N 33/52 | (2006.01) |
| G01N 33/533 | (2006.01) |
| C07F 9/655 | (2006.01) |
| B82Y 5/00 | (2011.01) |
| B82Y 10/00 | (2011.01) |
| B82Y 30/00 | (2011.01) |
| C07F 9/6558 | (2006.01) |
| G01N 33/58 | (2006.01) |

(Continued)

(52) U.S. Cl.
CPC ........ *C07F 9/65522* (2013.01); *C12Q 2334/20* (2013.01); *C12Q 1/42* (2013.01); *C12Y 301/03048* (2013.01); *B82Y 5/00* (2013.01); *B82Y 10/00* (2013.01); *B82Y 30/00* (2013.01); *C07F 9/65586* (2013.01); *G01N 33/573* (2013.01); *G01N 33/582* (2013.01)

(58) Field of Classification Search
CPC ... C07F 9/65522; C07F 9/65586; C12Q 1/42; C12Q 2334/20; C12Y 301/03048; G01N 33/573; G01N 33/582
See application file for complete search history.

(56) References Cited

U.S. PATENT DOCUMENTS

| | | | |
|---|---|---|---|
| 5,998,593 A * | 12/1999 | Huff et al. | 536/4.1 |
| 2002/0068301 A1* | 6/2002 | Lai et al. | 435/7.1 |
| 2005/0100951 A1* | 5/2005 | Pircher | 435/6 |

FOREIGN PATENT DOCUMENTS

| | | |
|---|---|---|
| WO | 01/94332 | 12/2001 |
| WO | 03/070174 | 8/2003 |
| WO | 2005/075488 | 8/2005 |

OTHER PUBLICATIONS

Gee et al (1999 Analytical Biochemistry 273:41-48).*
(Continued)

*Primary Examiner* — Christopher M Babic
*Assistant Examiner* — Jeremy C Flinders
(74) *Attorney, Agent, or Firm* — DLA Piper LLP (US)

(57) ABSTRACT

The design, synthesis, and utilization of a novel coumarin-based amino acid and its fluorinated derivatives for use in enzyme activity and substrate specificity assays are described. The synthesis is both facile and high-yielding and allows for the production of a highly fluorescent phosphorylated amino acid that can be incorporated into peptides using standard SPPS techniques. The resultant substrates are efficiently hydrolyzed by PTPs and exhibit a large increase in fluorescence upon hydrolysis. Fluorinated CAP derivatives have utility as fluorogenic enzyme substrates. CAP and its derivatives can be incorporated into combinatorial peptide libraries for assaying enzyme substrate specificities.

12 Claims, 8 Drawing Sheets

(51) Int. Cl.
G01N 33/573 (2006.01)
C12Q 1/42 (2006.01)

(56) References Cited

OTHER PUBLICATIONS

Daum et al (1993 Analytical Biochemistry 211:50-4).*
Lee et al (2003 Bioorganic & Medicinal Chemistry Letters 13:2577-81).*
Wang Resin product information sheet (2003).*
Petrassi et al. (Bioorganic & Medicinal Chemistry Letters, 2005, 15:3162-3166).*
Paschalidou, et al., "Highly Sensitive Intramolecularly Quenched Fluorogenic Substrates for Renin Based on the Combination of L-2-amino-3-(7-methoxy-4-coumaryl) propionic acid with 2, 4-dinitrophenyl groups at various positions", Biochemical Journal (2004) 382, pp. 1031-1038.
O'Donnell, et al., "solid-Phase Unnatural Peptide Synthesis" Journal of American Chemical Society (1996), 118 6070-6071.
Brun, et al., "A Very Short Route to Enantiomerically Pure Coumarin-Bearing Fluorescent Amino Acids" 2004, Angewandte Chemie, Eiley-VCH, Weinheim, DE, pp. 3432-3436.
Mitra, et al., "Highly Sensitive Peptide-Based Probes for Protein Tyrosine Phosphatase Activity Utilizing a Fluorogenic Mimic of Phosphotyrosine" Bioorganic & Medicinal Chemistry Letters, 15 (2005) pp. 5142-5145.

* cited by examiner ized as a fluorescent tag, they cannot be used as a substrate of an enzyme to evaluate its activity and substrate specificity.

COUMARIN-BASED AMINO ACIDS FOR USE IN ENZYME ACTIVITY AND SUBSTRATE SPECIFICITY ASSAYS

CROSS-REFERENCE TO RELATED APPLICATIONS

The present application claims priority to U.S. Provisional Patent Application Ser. No. 60/703,942, filed on Jul. 27, 2005.

FIELD OF THE INVENTION

The present invention relates to the design, synthesis, and utilization of a novel coumarin-based amino acids and their fluorinated derivatives for use in enzyme activity and substrate specificity assays.

BACKGROUND OF THE INVENTION

In the post-genomics era, the rate of data generation is far outpacing scientists' ability to analyze them. In the area of protein function and interactions, there is an ever-expanding catalog of posttranslational modifications and an analogous library of enzymes catalyzing the corresponding transformations to be studied. Many of these enzyme-substrate interactions are believed to play key roles in mediation diseases processes. Therefore, a proper understanding of the interactions between the enzymes and their cognate substrates promises to provide fundamental breakthroughs for new treatments and therapies. However, to study these interactions, it is of critical importance to have efficient tools that can readily identify from among many possible substrate candidates the biologically relevant substrates and measure the enzymatic activities of the enzymes. In the past, the lack of such tools has greatly hindered progress in our understanding of these fundamental biological processes.

In recent decades, fluorescent probes have emerged as a very useful class of research tool for biological and biochemical research. They are particularly useful in enzyme assays and the study of molecular trafficking and interactions. For example, fluorescein is commonly attached to biologically active molecules (e.g. antibodies) as a tag to track the movements of these molecules. Other fluorogenic and calorimetric substrates have also been used to assay protease activity and substrate specificity (Neefies et al., *Nature Rev. Drug Discovery* 3, 58-69 (2004), the entire content of which is incorporated herein in by reference) and have been used to a lesser extent to assay the activity of many other enzymes including glycosidases, phosphatases, sulfatases and esterases (Haugland, R. P. *Handbook of Fluorescent Probes and Research Products*, Molecular Probes Inc., Eugene, Oreg., 2002; Baruch et al., *Trends in Biotech*, 14, 29-35 (2004), the relevant portions of which are incorporated herein by reference).

Despite their increasing popularity, there remain many limitations to flouorescent probes. As a general rule, no fluorescent probes are universally applicable and different types of probes must be developed to meet different application requirements. For instance, the above-mentioned fluorescent tags, while useful as molecular beacons, have several major limitations for studying enzymatic activities. One major disadvantage is that attaching a bulky molecule such as fluorescein to a protein may disrupt the protein's native conformation, thereby, disrupting the very interaction which the experiment attempts to observe. Furthermore, many substrates of enzymes are peptides. Often, the functional groups of a peptide suitable for making covalent attachment to the fluorescent tags (e.g. the N and C termini, the carboxyl group of Asp side-chain, etc.) are also important in interacting with the enzyme. This poses a difficult challenge for adding fluorescent tags to peptide substrates, as attachment of the fluorescent tags would likely interfere with the native interactions of the peptides. Thus, there still exists a need for more adaptable fluorogenic probes that can easily be incorporated into peptides with minimal structural and activity impact for probing enzymatic activities (Goddard et al., *Trends in Biotech*, 22, 363-370 (2004), the entire content of which is incorporated herein by reference).

One excellent example of a family of enzymes whose study would greatly benefit from such a probe is the protein tyrosine phosphatase (PTP) enzyme family. The PTPs are a diverse family of enzymes involved in key signaling pathways and have been implicated in a number of disease states (Zhang et al., *PNAS*, 90, 4446-4450 (1993); Alonso et al., *Cell*, 117, 699-711 (2004), the relevant portions of which are incorporated herein by reference). Recent work indicates that PTPs have distinct substrate specificities, but a detailed understanding has been slow to emerge because the chemical tools necessary for studying PTP activity against peptide substrates were not available. Up until recently, assays for phosphatase activities have employed fluorogenic substrates based on para-nitrophenylphosphate (pNPP) and 4-methylumbelliferone (4-MU). These substrates suffer from the problem that maximum fluorescence of the reaction product requires an alkaline pH, thus, their sensitivity are highly influenced by the pH and prone to error (Montalibet et al., *Methods*, 35, 2-8 (2005), the entire content of which is incorporated herein by reference).

Alternative approaches such as mass-spectroscopy (Wang et al., *Biochem.*, 41, 6202-6210 (2002), the entire content of which is incorporated herein by reference) and protease-coupled assays (Nishikata et al., *Biochem. J.* 343, 385-391 (1999), the entire content of which is incorporated herein by reference) have been reported in the art. These approaches, while more accurate than measuring the fluorescence changes in the dephosphorylation of phosphotyrosine, requires expensive equipment, laborious preparation of samples, and cannot be used to monitor the activity of an enzyme on a continuous basis.

In spite of the various approaches described above, to date, there is no method for assaying PTP activity that is highly sensitive, fast, continuous, and relatively easy to perform. Thus, the development of a tool that can meet these requirements is highly desirable.

SUMMARY OF THE INVENTION

In view of the foregoing, several recent developments have been made in the prior art to advance the state-of-the-art. The prior art reference Gee at al. (U.S. Pat. No. 5,830,912) discloses several fluorinated coumarin derivatives, including DiFMUP and DIFUG. These compounds have reduced pH sensitivity and represents an improvement over the commonly used non-fluorinated coumarin-based fluorescent substrates for applications at physiological or acidic pH environments. However, the compounds of Gee et al. still suffer from the problem of not being able to be incorporated into peptides and suitable only as standalone substrates or extrinsic fluorescent labels.

Garbay et al. have disclosed a coumarin-based amino acid that can be directly incorporated into a peptide as an intrinsic fluorophore. However, The coumaryl amino acids of Garbay et al. do not have substituents that allow their fluorescence properties to be modulated directly by enzymes, thus, while they represent an improvement over prior art fluorescent labels such as fluorescein or the coumarin-based derivatives of Gee et al., they lack the capability of acting as a reporter and, therefore, are not ideal probes for enzymatic activities.

In one aspect, the present invention provides a set of novel coumaryl amino acids that can readily be incorporated into peptides and that are also capable of acting as reporters in enzymatic assays. These compounds may comprise various substituents that may modulate their physical and chemical properties including, for example, their solubilities, reactivities, and fluorescence properties. In another aspect, the present invention also provides novel methods for assaying, detecting, and profiling enzymes utilizing these compounds. In still another aspect, the present invention provides methods for manufacturing these novel compounds with unexpectedly high yield and purity. Various other applications and methods for using these novel compounds have also been contemplated.

Accordingly, in one aspect, the present invention provides coumary amino acids having the general formula:

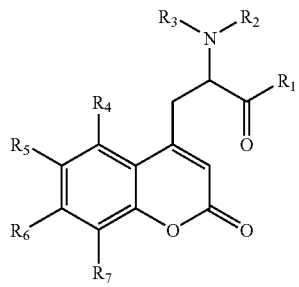

wherein, $R_1$ is a functionality selected from the group consisting of OH, halogen, O-L, amide, peptide, O⁻, wherein L is one selected from alkyl, aryl, or a protecting group;

$R_2$ is a functionality selected from the group consisting of H, alkyl, aryl, peptide, carbamoyl, carboxyl, acyl, and a protecting group;

$R_3$ is a functionality selected from the group consisting of H, alkyl, aryl, peptide, carbamoyl, carboxyl, acyl, and a protecting group;

$R_4$ is a functionality selected from the group consisting of H, halogen, alkyl, aryl, ether, ester, nitrile, azide, thiol, thioether, OH, sulfate, phosphate, sulfonate, phosphonate, primary amine, secondary amine, tertiary amine, primary amide, secondary amide, carboxyl, and a carbamoyl functional group;

$R_5$ is a functionality selected from the group consisting of H, halogen, alkyl, aryl, ether, ester, nitrile, azide, thiol, thioether, OH, sulfate, phosphate, sulfonate, phosphonate, primary amine, secondary amine, tertiary amine, primary amide, secondary amide, carboxyl, and a carbamoyl functional group;

$R_6$ is a functionality selected from the group consisting of OH, primary amine, secondary amine, tertiary amine, primary amide, secondary amide, peptide, aminophosphate, phosphoramidate, $OPO_3H_2$, $OPO_3^{2-}$, $OPO_3R_8R_9$, wherein $R_8$ and $R_9$ are independently selected from H, halogen, alkyl, aryl, ether, ester, nitrile, azide, thiol, thioether, OH, sulfate, phosphate, sulfonate, phosphonate, primary amine, secondary amine, tertiary amine, primary amide, secondary amide, carboxyl, or carbamoyl functional group.

$R_7$ is a functionality selected from the group consisting of H, halogen, alkyl, aryl, ether, ester, nitrile, azide, thiol, thioether, OH, sulfate, phosphate, sulfonate, phosphonate, primary amine, secondary amine, tertiary amine, primary amide, secondary amide, carboxyl, and a carbamoyl functionality, and wherein, when $R_6$ is selected from OH, primary amine, secondary amine, tertiary amine, primary amide, and secondary amide, $R_1$ and $R_2$ form a ring structure containing at least one atom on the ring selected from the group consisting of C, N, and O.

In one preferred embodiment, the coumarin moiety is fluorinated at the $R_5$ and/or $R_7$ position, wherein $R_5$ and $R_7$ are independently fluorinated.

In another preferred embodiment, $R_1$ and $R_2$ are peptides and $R_6$ is selected from the group consisting of peptide, aminophosphate, phosphoramidate, $OPO_3H_2$, $OPO_3^{2-}$, and $OPO_3R_8R_9$, wherein $R_8$ and $R_9$ are independently selected from H, halogen, alkyl, aryl, ether, ester, nitrile, azide, thiol, thioether, OH, sulfate, phosphate, sulfonate, phosphonate, primary amine, secondary amine, tertiary amine, primary amide, secondary amide, carboxyl, and carbamoyl functional group.

In yet another preferred embodiment, $R_1$ and $R_2$ form a ring structure containing at least one atom on the ring selected from the group consisting of C, N, and O. In a further embodiment, the ring structure may further comprise a peptide.

Advantageously, coumaryl amino acids according to embodiments of the present invention are easily incorporated into a peptide, provide superior fluorescent properties, and provide excellent thermal and chemical stability.

In those embodiments where $R_5$ and/or $R_7$ are fluorinated, a coumaryl amino acid of the present invention have an additional advantage of having a lowered pKa and improved fluorescent properties at neutral or acidic medium, rendering it better suited for biological applications.

In another preferred embodiment, $R_1$ and $R_2$ are peptides and $R_6$ is selected from the group consisting of peptide, aminophosphate, phosphoramidate, $OPO_3H_2$, $OPO_3^{2-}$, $OPO_3R_8R_9$, wherein $R_8$ and $R_9$ are independently selected from H, halogen, alkyl, aryl, ether, ester, nitrile, azide, thiol, thioether, OH, sulfate, phosphate, sulfonate, phosphonate, primary amine, secondary amine, tertiary amine, primary amide, secondary amide, carboxyl, and a carbamoyl functional group. This embodiment of a coumaryl amino acid provides an additional advantage of having a modulated fluorescence property, wherein upon removal or attachment of at least part of the $R_6$ substituent, the fluorescence intensity is modulated.

In those embodiments wherein $R_1$ and $R_2$ form a ring structure and wherein at least one atom on the ring is one selected from the group consisting of C, N, and O, and wherein the ring may further comprise a peptide, a coumaryl amino acid of the present invention will have at least the advantages of having both the N- and C-termini protected by the same moiety in which de-protection of both termini can be carried out in one single step. Further advantages include having a cyclic moiety that may be advantageously employed as probes for enzymes that act on cyclic peptides.

The inventors of the present invention have unexpectedly discovered that a coumaryl amino acid according to the various embodiments of the present invention is particularly suited to be incorporated into peptides as active probes, wherein the various possible combinations of substituents provide a rich set of chemistry to be adapted to a wide range of enzyme assay applications. For the purpose of this invention, the term "active probe" means that the fluorescent probe changes its fluorescence intensity upon interacting with the enzyme, as opposed to merely acting as a molecular beacon that fluoresces regardless of its interaction with an enzyme.

In another aspect, the present invention also provides a novel method for manufacturing a coumaryl amino acid comprising the general steps of:

(a) providing an amino acid derived β-ketoester;
(b) providing a substituted phenol;
(c) reacting said amino acid derived β-ketoester with said substituted phenol in the presence of an acid at a temperature range from about 0° C. to about 10° C.

In one preferred embodiment, the substituted phenol is non-substituted resorcinol. In another preferred embodiment, the substituted phenol is a fluorinated resorcinol.

The inventors of the present invention have unexpectedly discovered that a method according to one embodiment of the present invention wherein step (c) is carried out at a low temperature, preferably in the range of about 0° C. to about 10° C., more preferably from about 0° C. to about 4° C., results in an unexpectedly high yield and purity for a non-fluorinated coumaryl amino acid, wherein the yield is preferably greater than 80%, more preferably greater than 90%, and the purity is preferably greater than 90%.

It is known in the art that it is particularly difficult to achieve the condensation reaction between a fluorinated resorcinol and an amino acid derived β-ketoester. The inventors have unexpectedly discovered that in a method according to those embodiments of the present invention wherein the substituted phenol is a fluorinated resorcinol, a higher yield, preferably higher than 8%, more preferably about 52%, is obtained.

In yet another aspect, the present invention also provides a kit for assaying an enzyme comprising a coumaryl amino acid according to embodiments of the present invention.

In yet another aspect, the present invention also provides a peptide substrate library comprising a plurality of peptides, wherein at least one peptide in the library comprises one or more coumaryl amino acids according to embodiments of the present invention.

In some embodiments, at least one peptide of the library has a randomly generated sequence. In other embodiments, at least one peptide of the library has a predetermined sequence.

In yet another aspect, the present invention also provides a method for determining an activity of an enzyme, comprising the general steps of:

providing a coumaryl amino acid according to embodiments of the present invention;
contacting the compound with the enzyme; and
measuring a change in a fluorescent intensity of the compound, wherein the enzymatic activity of the enzyme is indicated by the change of the fluorescent intensity.

In yet another aspect, the present invention also provides a method for characterizing an enzyme activity, comprising the general steps of:

providing a peptide substrate library according to claim 19;
contacting the enzyme with the peptide substrate library; and
measuring a change in a fluorescence pattern of the library, wherein the change of pattern corresponds to a characteristic of the enzyme.

In yet another aspect, the present invention also provides a method for detecting one or more enzymes in a sample, comprising the general steps of:

providing a peptide substrate library, wherein
the library comprises at least one target peptide known to be recognized by at least one enzyme to be detected; and
the target peptide comprises one or more residues having a structural formula according to claim 1;
contacting the sample with the library; and
measuring a change in a fluorescence intensity of the target peptide,
wherein the change in the fluorescence intensity produced by the target peptide indicates that the target peptide is recognized by the enzyme.

Other aspects of the present invention further provide a composition comprising a coumaryl amino acid according to embodiments of the present invention and a biosensor also comprising a coumaryl amino acid of the present invention or a substrate library according to embodiments of the present invention.

The various aspects and embodiments of the present invention are further described in detail below.

DETAILED DESCRIPTION OF THE INVENTION

Figure 1:
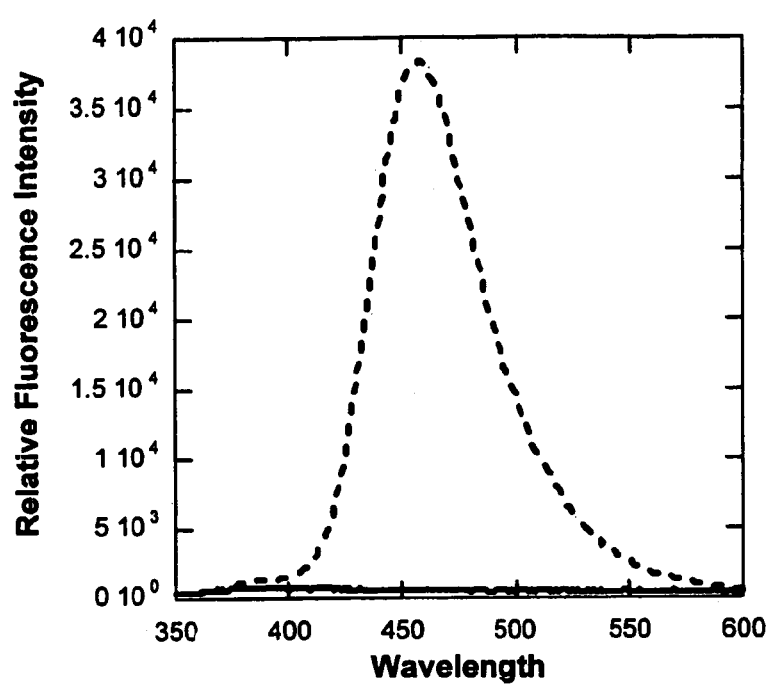
FIG. 1. Emission spectra of peptides 10a (solid line) and 10b (dashed line). Each peptide solution contained 22 μM peptide in the enzyme activity buffer. Excitation wavelength=334 nm.

The present invention may be understood more readily by reference to the following detailed description of the preferred embodiments of the invention, and to the examples included therein.

Novel Coumaryl Amino Acids and Derivatives:

Coumarins are interesting fluorescent molecules due to their relatively high quantum yield, low bleaching, and reasonable stability. Coumarin-based amino acids (or coumaryl amino acids) are, therefore, excellent candidates as intrinsic fluorescent labels for peptides and proteins. The invention provides novel coumarin-based amino acids and derivatives thereof that are useful for continuous assays of enzyme activities and enzyme-substrate interactions.

In one embodiment, a coumaryl amino acid according to the present invention has the general structural formula:

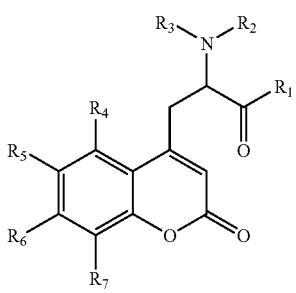

wherein:
- $R_1$ is a functionality selected from the group consisting of OH, halogen, O-L, amide, peptide, O⁻, wherein L is one selected from alkyl, aryl, or a protecting group;
- $R_2$ is a functionality selected from the group consisting of H, alkyl, aryl, peptide, carbamoyl, carboxyl, acyl, and a protecting group;
- $R_3$ is a functionality selected from the group consisting of H, alkyl, aryl, peptide, carbamoyl, carboxyl, acyl, and a protecting group;
- $R_4$ is a functionality selected from the group consisting of H, halogen, alkyl, aryl, ether, ester, nitrile, azide, thiol, thioether, OH, sulfate, phosphate, sulfonate, phosphonate, primary amine, secondary amine, tertiary amine, primary amide, secondary amide, carboxyl, and a carbamoyl functional group;
- $R_5$ is a functionality selected from the group consisting of H, halogen, alkyl, aryl, ether, ester, nitrile, azide, thiol, thioether, OH, sulfate, phosphate, sulfonate, phosphonate, primary amine, secondary amine, tertiary amine, primary amide, secondary amide, carboxyl, and a carbamoyl functional group;
- $R_6$ is a functionality selected from the group consisting of OH, primary amine, secondary amine, tertiary amine, primary amide, secondary amide, peptide, aminophosphate, phosphoramidate, $OPO_3H_2$, $OPO_3^{2-}$, $OPO_3R_8R_9$, wherein $R_8$ and $R_9$ are independently selected from H, halogen, alkyl, aryl, ether, ester, nitrile, azide, thiol, thioether, OH, sulfate, phosphate, sulfonate, phosphonate, primary amine, secondary amine, tertiary amine, primary amide, secondary amide, carboxyl, or carbamoyl functional group.
- $R_7$ is a functionality selected from the group consisting of H, halogen, alkyl, aryl, ether, ester, nitrile, azide, thiol, thioether, OH, sulfate, phosphate, sulfonate, phosphonate, primary amine, secondary amine, tertiary amine, primary amide, secondary amide, carboxyl, and a carbamoyl functionality, and wherein,
when $R_6$ is selected from the group consisting of OH, primary amine, secondary amine, tertiary amine, primary amide, and secondary amide, $R_1$ and $R_2$ form a ring structure containing at least one atom on the ring selected from the group consisting of C, N, and O.

For the purpose of this invention, an alkyl group is preferably between 1-18 carbons, more preferably between 1-5 carbons. Examples of an alkyl group include, but are not limited to methyl, ethyl, propyl, isopropyl, butyl, isobutyl, t-butyl, pentyl, isopentyl, neopentyl, cyclopropyl, cyclobutyl, and cyclopentyl.

Examples of an aryl group include, but not limited to benzene, toluene, and xylene.

Examples of a protecting group suitable for use in $R_1$ may include trichloroethanol (Tce), methoxymethyl (MOM), 2-(trimethylsilyl)ethyl (TMSE), 3-methylbut-2-enyl (Prenyl), pentafluorophenyl (Pfp), or any other protecting groups commonly known to those skilled in the art as suitable for protecting carboxyl terminus.

Examples of a protecting group suitable for use in $R_2/R_3$ may include 9-fluorenylmethyl (Fmoc), t-butyl (Boc), N-trifluoroacetyl (TFA), N-o-(benzoyloxymethyl)benzoyl (BMB), N-benzyl (Bn), N-diphenylphosphinyl (Dpp), or any other protecting groups commonly known to those skilled in the art as suitable for protecting amine terminus.

Peptides are preferably between 1 to 100 residues long, more preferably between 1 to 10. The sequence of the peptides may be randomly selected or predetermined.

Examples of a carbamoyl group may include, but not limited to 9-fluorenylmethyl (Fmoc).

Examples of a carboxyl group, as used in $R_2$-$R_7$, may include but not limited to COOH.

Examples of an acyl may include, but not limited to $COCH_3$.

Examples of an ether and ester may include, but not limited to methyl ether or methyl ester.

Accordingly, Table 1 shows coumaryl amino acids according to some embodiments of the present invention.

TABLE 1

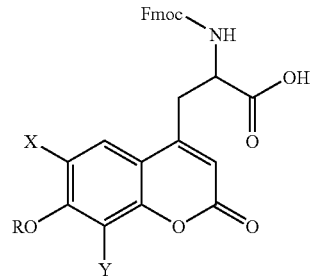

R = H, X = Y = H
R = H, X = H, Y = F
R = H, X = Y = F
R = CH₃, X = Y = H
R = PO(OEt)₂, X = Y = H
R = PO(OEt)₂, X = H, Y = F
R = PO(OEt)₂, X = Y = F

In a further embodiment, the amino acid moiety may be in a cyclic form having the general structural formula:

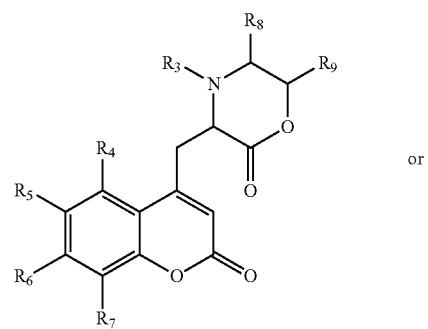

or

-continued

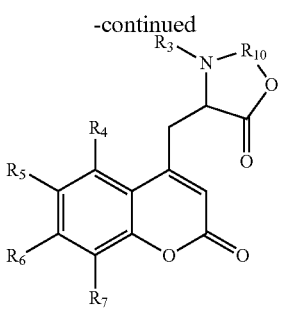

wherein $R_3$-$R_9$ are as defined above and $R_{10}$ represents the remainder of the ring structure containing at least one of the following: C, N, O. In yet another further embodiment, $R_{10}$ may also be a cyclic peptide containing one or more natural or unnatural amino acids.

Accordingly, Table 2 shows coumaryl amino acids according to further embodiments of the present invention.

TABLE 2

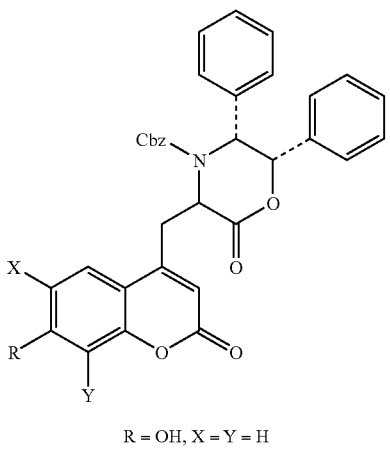

R = OH, X = Y = H
R = OH, X = H, Y = F
R = OH, X = Y = F
R = PO(OEt)$_2$, X = Y = H
R = PO(OEt)$_2$, X = H, Y = F
R = PO(OEt)$_2$, X = Y = F

In a further embodiment, the compound may additionally comprise one or more counter ion(s) to form a salt. The counter ion(s) may be an organic or inorganic. Examples of an organic ion include, but not limited to triflate, tosylate, tetraphenyl borate, and tetrabutyl ammonium. Examples of an inorganic ion include, but not limited to sodium, potassium, calcium, chloride, and iodide.

Novel Synthetic Scheme

To manufacture the novel coumaryl amino acids according to the various embodiments of the present invention, the inventors have invented a novel synthetic scheme that is capable of producing the coumaryl amino acids in high global yield and enantiomerically purity.

In general, the synthetic scheme of the present invention comprises the steps of:
(a) providing an amino acid derived β-ketoester;
(b) providing a substituted phenol;
(c) reacting said amino acid derived β-ketoester with said substituted phenol in the presence of an acid solution at a temperature range from about −5° C. to about 10° C., preferably from about 0° C. to about 4° C.

Examples of the amino acid derived β-ketoester may include, but not limited to [2-(9H-Fluoren-9-ylmethoxycarbonylamino)-4-oxo-hexanedioic acid 6-methyl ester 1-(2,2,2-trichloro-ethyl)ester, 2-(9H-Fluoren-9-ylmethoxycarbonylamino)-5-oxo-heptanedioic acid 7-methyl ester 1-trichloromethyl ester, 2-Amino-4-oxo-hexanedioic acid 6-methyl ester, 2-Amino-5-oxo-heptanedioic acid 7-methyl ester]. Preferably, the amino acid derived β-ketoester is [2-(9H-Fluoren-9-ylmethoxycarbonylamino)-4-oxo-hexanedioic acid 6-methyl ester 1-(2,2,2-trichloro-ethyl)ester. Examples of the acid solution may include, but not limited to a solution comprising methanesulfonic acid and dichloromethane, and a solution comprising toluenesulfonic acid and dichloromethane. The substituted phenol may be one selected from the group consisting of resorcinol, fluororesorcinol, and difluororesorcinol.

In those embodiments where methanesulfonic acid in dichloromethane is used, the concentration of methanesulfonic acid is preferably between 1% and 100%, and more preferably either between 1% and 5% or 100%. In those embodiments where toluenesulfonic acid in dichloromethane is used, the concentration of the acid is preferably between 1% and 5%, and more preferably between 1% and 2%.

The inventors have unexpectedly discovered that when step (c) is carried out at low temperature, a surprisingly higher yield is obtained. In those embodiments where the substituted phenol is non-substituted resorcinol, the yield of the coumaryl acid is at least 60%, more preferably 70%-88%. In those embodiments where the resorcinol is fluorinated, the yield of the coumaryl acid is at least 10%, more preferably 10-55%.

The inventors have also unexpectedly discovered that when neat (100%) methanesulfonic acid is used in conjunction with the low temperature condition, a much better result is obtained.

In a further embodiment, a method of the present invention further comprises the step of adding diisopropylethylamine and diethylechlorophosphate to the product of step (c) to form a phosphorylated coumaryl amino acid.

The method of the present invention may be used to manufacture coumaryl amino acids in general. In particular, the method of the present invention as set forth here may advantageously be used to manufacture the novel coumaryl amino acids of the present invention.

In one exemplary embodiment, a method for manufacturing the novel coumaryl amino acids of the present invention comprises the following synthetic steps:
1. An enantiomerically pure L-aspartic acid β-ester is used as the chiral starting material. The β-carboxylic acid should have a protecting group such as tertiary butyl or any other suitable protecting group commonly known in the art. The amine group of the amino acid should also have a protecting group such as Fmoc or any other suitable protecting groups commonly known in the art.
2. The α-carboxylic acid is first protected by a protecting group such as trichloroethyl (Tce) ester or other suitable protecting group commonly known in the art.
3. Once the α-carboxylic acid is protected, the β-carboxylic acid is then deprotected and acylated. The acylation reaction is preferably carried out using isopropenyl chloroformate and Meldrum's acid, but may also be carried out with other suitable reagents and reaction conditions commonly known in the art.
4. To form the coumaryl moiety, the amino acid derived β-ketoester is reacted with a substituted phenol, preferably resorcinol, in the presence of methanesulfonic acid (MSA). Huyer et al. has recently reported that MSA may act as a catalyst to catalyze the condensation reaction between an amino acid derived β-ketoester and resorcinol at room temperature (*Anal. Biochem.* 19, 258, (1998), the entire content of which is incorporated herein by reference). This reaction has been shown to preserve the stereocenter of the resulting product. The inventors have unexpectedly discovered that when carried out at from about −5° C. to about 10° C., the condensation reaction gives substantially higher yields of the N- and C-protected coumaryl amino acids as compared with the same reaction carried out at room temperature. In one embodiment of the present invention, the condensation reaction was carried out at 0-4° C.

5. The hydroxyl group on the coumaryl moiety may be further derivatized with other functionalities. For example, phosphorylation of the coumaryl moiety may be achieved by diethychlorophosphate and diisopropylethylamine to give a phosphorylated coumaryl amino acid. Those of ordinary skill in the art will recognize that derivatization of the coumaryl amino acid with other functionalities such as amide or peptide are also possible via standard hydroxyl group chemistry commonly known in the art.

6. Finally, the protecting groups may be removed using appropriate chemistry corresponding to the protecting group. For example, when the protecting group is Fmoc, 2% diaza(1,3)bicyclo[5.4.0]undecane (DBU) in dichloromethane may be used to remove the protecting group.

Diagram 1 below illustrates a synthetic scheme according to one embodiment of the present invention. For the sake of brevity, the term CAP will henceforth be used to refer to a coumaryl amino acid having the structural formula 6 shown below with the protecting group Tce replaced with H. The terms pCAP, pCAPF, and pCAPF2 are as defined by the structural formula shown below (8a-8c).

(iv) $CH_3SO_3H$ 0° C., 6 hours, 60% yield
(v) $(EtO)_2POCL$, diisopropylethylamine, $CHCl_3$, room temperature, 14 hours, 85% yield
(vi) Zinc dust (6 equivalent) 50% acetic acid in THF, room temperature, 8 hours, 99% yield.

Peptide Substrate Library

The present invention also provides a peptide substrate library utilizing the novel coumaryl amino acids of the present invention. In general, a peptide substrate library of the present invention comprises a plurality of peptides, wherein at least one peptide in the library comprises one or more novel coumaryl amino acid(s) of the present invention, and wherein said peptide is at least two residues long. Preferably, the lengths of the peptides are between 2 and 100 residues, and more preferably, between 2 and 10.

The novel coumaryl amino acids may be incorporated into a peptide chain at any position along the sequence. Synthesis of the peptides may employ any peptide synthesis method commonly known in the art or any future methods so long as it is capable of accommodating the novel coumaryl amino acids of the present invention and any other natural or non-natural amino acids. Examples of commonly used peptide synthesis methodologies include, but not limited to solid phase peptide synthesis (SPPS) methodologies, solution phase peptide synthesis methodologies, and automated peptide synthesis methodologies. Examples of non-natural amino acids may include, but not limited to norleucine, beta-alanine, homoserine and allylglycine.

In some embodiments, the sequence of the peptides may be randomly generated. In other embodiments, the sequences may be predetermined. In still other embodiments, the library may comprise all possible peptide sequences for a predetermined number of residues and types of residues. In those embodiments where some sequences are predetermined, many methods for selecting the sequences are possible,

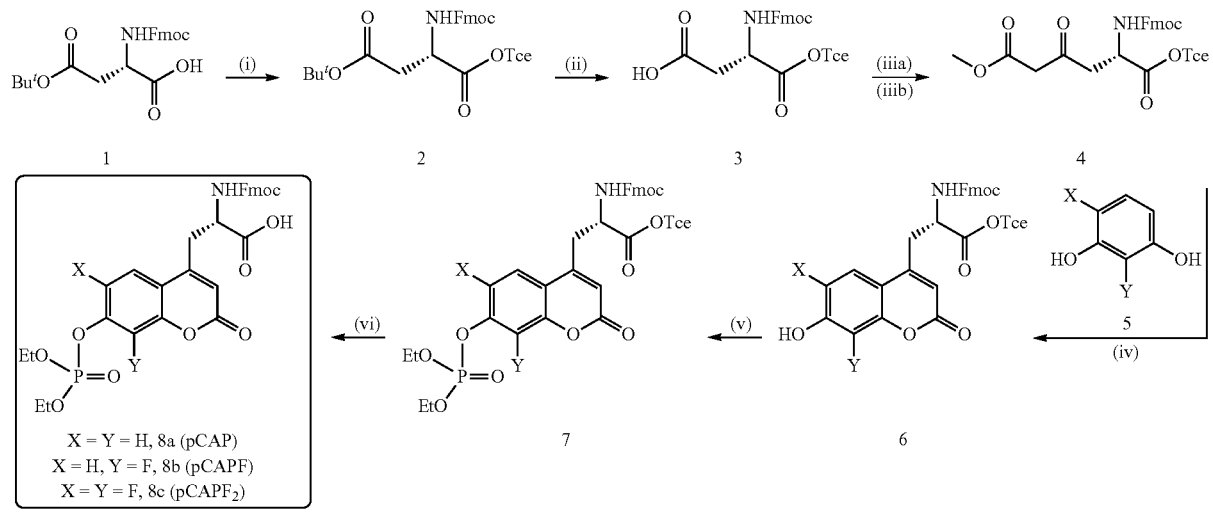

Diagram 1

(i) $CCl_3CH_2OH$, dicyclohexylcarbodiimide, DMAP, 0° C., 15 hours, 97% yield;
(ii) 50% TFA in $CH_2Cl_2$, room temperature, 15 min, >>99% yield;
(iiia) Isopropenyl chloroformate, Meldrum's acid, DMAP, $CH_2Cl_2$, 0° C., 2 hours
(iiib) $CH_3OH$/benzene (4:1), reflux, 12 hours, 94% depending on the need of a particular application. For example, a sequence may be selected based on a sequence-enzyme specificity correlation. Other methods for predetermining the sequences may include, but not limited to bioinformatics-based selection schemes.

In some embodiments, at least one peptide of the library may comprise a sequence corresponding to a sequence recognized by an enzyme. For the purpose of this invention, a recognition event is one in which a host molecule (enzyme) is able to form a complex with a second guest molecule (peptide). This process occurs through non-covalent chemical bonds including hydrogen bonding, hydrophobic interactions, ionic interaction, or other interactions between the two molecules. Examples of some enzymes may include, but not limited to phosphatase, kinase, amidase, peptidase, protease, glycosidase and sulfatase. In still some embodiments, the enzyme is preferably a protein tyrosine phosphatase. In yet still some other embodiments, the enzyme is a protein tyrosine kinase.

In some embodiments, the library may further comprise a solid support. Some examples of a suitable solid support may include, but not limited to glass solid support, plastic, metal, ceramic and semiconducting material.

In some embodiments, at least one peptide of the library is attached to a bead. Examples of a suitable bead may include, but not limited to polystyrene, polyethylene, glass, gold, DEAE, PEGA, magnetic metal, and quantum dots. A peptide library according to this embodiment of the present invention may have, but not limited to, the following advantages: attaching such a bead to a peptide may providing a stabilizing support, a means for identification, or a means for physical separation manipulation. The sizes of these beads are preferably from about 5 to about 500 microns, and more preferably from about 100 to 300 microns.

Applications and Method of Use

In one aspect, the present invention provides a method for determining an activity of an enzyme, comprising the general steps of:

providing a coumaryl amino acid capable of interacting with an enzyme;

contacting the coumaryl amino acid with the enzyme; and measuring a change in a fluorescent intensity of the compound, wherein the enzymatic activity of the enzyme is indicated by the change of the fluorescent intensity.

In some embodiments, the coumaryl amino acid preferably has a substituent that is capable of being acted on by the enzyme, wherein the enzyme may act to either remove or attach the substituent to the coumaryl amino acid. In a further embodiment, the act of removing or attaching is covalently removing or attaching. In another further embodiment, the removing or attaching is limited only to a portion of the substituent. In some embodiments, when the substituent is removed or attached, a detectable change in the fluorescence property of the coumaryl amino acid is effected.

Although embodiments of the present invention employs change in fluorescence intensity as an indicator, other types of changes are also contemplated. Examples of changes may include, but not limited to a loss or increase of fluorescence intensity at one or more wavelengths, a colorimetric alternation, and a change in pKa.

Examples of suitable substituent that may be acted upon by an enzyme may include, but not limited to those disclosed for $R_6$.

Examples of enzyme activities to be determined may include, but not limited to binding affinity, substrate specificity, and turnover rate.

Examples of enzymes may include, but not limited to a phosphatase, kinase, amidase, peptidase, protease, glycosidase and a sulfatase.

In one embodiment, the coumaryl amino acid is one selected from a novel coumaryl amino acid of the present invention. In another embodiment, the coumaryl amino acid may further comprise peptides with sequences known to be recognized by the enzyme.

In another aspect, the present invention also provides a novel method for characterizing an enzyme, comprising the general steps of:

providing a peptide substrate library according to the present invention;

contacting the enzyme with the peptide substrate library; and measuring a change in a fluorescence pattern of the library, wherein the change of fluorescence pattern of the library forms a characteristic profile of the enzyme.

Examples of enzymes that may be characterized by methods according to some embodiments of the present invention may include, but not limited to phosphatase, kinase, amidase, peptidase, protease, glycosidase and sulfatase.

Examples of the profiled characteristic may include, but not limited to binding affinity, substrate specificity, and turnover rate.

In some embodiments, the method may further comprise determining a correlation between the change of fluorescence and a molecular property of at least one peptide in the library. Examples of molecular properties may include, but not limited to structural, sequence, electrostatics, molecular weight, conformation, and combinations thereof.

In yet another aspect, the present invention provides a method for designing enzyme inhibitors. In one embodiment, the method comprises obtaining a characteristic profile of the enzyme and using an enzyme characterizing method according to some embodiments of the present invention as set forth above, determining a correlation between the change of fluorescence and a molecular property of at least one peptide in the library; and designing an inhibitor based on the correlation.

In yet another aspect, the present invention also provides a method for detecting one or more enzymes in a sample. Embodiments according to this aspect of the present invention may comprise the general steps of:

providing a peptide substrate library, wherein the library comprises at least one target peptide known to be recognized by at least one enzyme to be detected;

and the target peptide comprises one or more novel coumaryl amino acid of the present invention;

contacting the sample with the library; and measuring a change in a fluorescence intensity of the target peptide, wherein the change in the fluorescence intensity produced by the target peptide indicates that the target peptide is recognized by the enzyme.

In yet another aspect, the present invention also provides a biosensor. In some embodiments, the biosensor may comprise a sensing element wherein the sensing element may comprise a peptide substrate library of the present invention or a coumaryl amino acid of the present invention.

In yet another aspect, the present invention also provides a composition comprising a novel coumaryl amino acid of the present invention.

In yet another aspect, the present invention also provides kits for performing methods according to the various embodiments of the present invention. In some embodiments, a kit of the present invention may comprise a novel coumaryl amino acid of the present invention. In other embodiments, a kit of the present invention may comprise a peptide substrate library according to the present invention.

The following examples are intended to illustrate, but not to limit, the scope of the invention. While such examples are typical of those that might be used, other procedures known to those skilled in the art may alternatively be utilized. Indeed, those of ordinary skill in the art can readily envision and produce further embodiments, based on the teachings herein, without undue experimentation.

EXAMPLES

Materials

Protein tyrosine phosphatase from *Yersinia enterocolitica* (YOP)[16] and human T-cell PTP (TCPTP)[17] were obtained from Calbiochem in purified form and used as received. Reagents for solid phase peptide synthesis including Fmoc protected amino acids and Rink Amide resin were obtained from Novabiochem and used without further purification. Trichloroethanol (TCE), resorcinol, dicyclohexylcarbodiimide (DCC) and N,N-dimethylaminopyridine (DMAP) were obtained from Lancaster, isopropenyl chloroformate (IPCF) from Acros Organics, trifluoroacetic acid (TFA) from Oakwood Chemicals and methanesulfonic acid, diethyl chlorophosphate and zinc dust were obtained from Aldrich Chemical Company. Dry solvents were obtained from VWR and Aldrich. Fluorinated resorcinols were synthesized according to a literature procedure.[18] All of the chemicals were used as received, except zinc, which was activated prior to use by washing with 20% HCl, followed by water and acetone.

$^1$H, $^{13}$C, and $^{31}$P NMR spectra were recorded on Bruker AC 250, Bruker AC 360 and Varian 400 MHz instruments. Peptides were purified on a Varian ProStar 210 HPLC system using a preparative-scale C18 reverse-phase column. Mass spectrometric characterization was carried out using an Applied Biosystems Voyager-DE STR MALDI-TOF instrument with α-cyanohydroxycinnamic acid as the matrix. Enzyme assays with fluorogenic substrates were performed on a Molecular Devices Analyst AD multimode plate reader in fluorescence mode with an excitation filter, emission filter and dichroic mirror at 360 nm, 425 nm, and 400 nm, respectively. Enzymatic hydrolysis of the phosphotyrosine-containing peptide DADE-phpsphotyrosine-GPAA (9a) was followed by observing an increase in absorbance at 280 nm using a Varian Cary50 spectrophotometer. FIG. 1 shows a fluorescence spectra of the coumaryl amino acids and peptides DADE-pCAP-GPAA (10a) and DADE-CAP-GPAA (10b) were obtained by using a Jobin-Yvon Horiba Fluoromax-3.

A. Synthesis of Phosphorylated Coumaryl Amino Acid

In the following examples, compounds 1-8 correspond to the compound numbers shown in Diagram 1.

Example 1

Synthesis of 2-(9H-Fluoren-9-ylmethoxycarbonylamino)-succinic acid 4-tert-butyl ester 1-(2,2,2-trichloro-ethyl)ester (2)

A solution of compound 1 (0.4115 g, 1 mmol), 2,2,2-trichloroethanol (1.3 equiv) and DMAP (0.5 equiv) in anhydrous dichloromethane was cooled to –78° C. To this mixture, DCC (1.3 equiv) was added and the reaction mixture was allowed to stir at –78° C. for 2 h. Upon completion of the reaction, the precipitates were filtered and filtrate diluted with ethyl acetate (20 mL). The resulting solution was washed sequentially with 10% aqueous citric acid, water, saturated NaHCO$_3$, water and brine. The solvent was evaporated, producing 2 as a white solid. The compound was purified by column chromatography over silica gel (60-200 mesh) eluting with (4:1) cyclohexane/ethyl acetate to yield 0.526 g (97%) 2 as a white solid. Alternately, the dicyclohexyl urea present as impurity in the compound can be removed without doing a column by dissolving the crude product in minimum amount of ethyl acetate and leaving in an acetone/dry ice bath at –78° C. for 2 h, followed by filtration of the urea and washing with cold ethyl acetate. $^1$H NMR (CDCl$_3$, TMS, 400 MHz) δ 7.68 (d, J=7.5, 2H), 7.52 (d, J=7.25, 2H), 7.32 (t, J=7.25, 2H), 7.23 (t, J=7.25, 2H), 5.30 (d, J=8.75, 1H), 4.77 (d, J=11.7, 1H), 4.70 (m, 1H), 4.64 (d, J=11.7, 1H), 4.32 (m, 2H), 4.16 (t, J=7.0, 1H), 2.85-2.94 (A part of an ABX system, $J_{AB}$=12.8, $J_{AX}$=5.2, 1H), 2.72-2.74 (B part of an ABX system, $J_{AB}$=12.8, $J_{BX}$=5.2, 1H), 1.37 (s, 9H). $^{13}$C NMR (CDCl$_3$, TMS, 100 MHz) δ 170.04, 169.68, 156.12, 143.89. 143.73, 141.38, 127.82 (×2), 127.15 (×2), 125.23 (×2), 120.10 (×2), 94.43, 82.32, 74.89, 67.50, 50.46, 47.13, 37.55, 28.14. MS (MALDI/TOF) [C$_{25}$H$_{26}$NO$_6$Cl$_3$+Na]$^+$: Calculated: 564.07 (100%), 566.07 (96%). Found: 564 (100%), 566 (96%)

Example 2

Synthesis of 2-(9H-Fluoren-9-ylmethoxycarbonylamino)-succinic acid 1-(2,2,2-trichloro-ethyl)ester (3)[19]

A solution of 2 in dichloromethane (4 mL) was treated with an equal volume of trifluoroacetic acid (TFA). The resulting mixture was allowed to stir at room temperature for 15 min. The solvent was then evaporated under reduced pressure and the compound 3 precipitated by addition of water (10 mL). The precipitate was filtered through a Buchner funnel, and dried to obtain 0.47 g of 3 as a white solid in quantitative yield. $^1$H NMR (CDCl$_3$, TMS, 400 MHz) δ 7.76 (d, J=7.2, 2H), 7.60 (d, J=7.2, 2H), 7.41 (t, J=7.2, 2H), 7.32 (t, J=7.2, 2H), 5.87 (d, J=8.8, 1H), 4.81 (d, J=12, 1H), 4.77 (m, 1H), 4.73 (d, J=12, 1H), 4.42-4.46 (A part of an ABX system, $J_{AB}$=2.8, $J_{AX}$=7.6 Hz), 4.33-4.37 (B part of an ABX system, $J_{AB}$=2.8, $J_{BX}$=7.6, 1H), 4.23 (t, J=7.2, 1H), 3.12-3.17 (A part of an ABX system, $J_{AB}$=17.6, $J_{AX}$=4.4, 1H), 2.96-3.01 (B part of an ABX system, $J_{AB}$=17.6, $J_{BX}$=4.4, 1H). $^{13}$C NMR (CDCl$_3$, TMS, 63 MHz) δ 175.37, 169.32, 156.21, 143.85, 143.74, 141.49, 127.98(×2) 127.30(×2), 125.26(×2), 120.22 (×2), 94.40, 77.20, 75.05, 67.71, 50.28, 47.21, 36.29. MS (MALDI/TOF) [C$_{21}$H$_{18}$NO$_6$Cl$_3$+Na]$^+$: Calculated: 508.01 (100%), 510.01 (97%). Found: 508 (100%), 510 (95%).

Example 3

2-(9H-Fluoren-9-ylmethoxycarbonylamino)-4-oxohexanedioic acid 6-methyl ester 1-(2,2,2-trichloroethyl)ester (4)[20]

A solution of 3 (0.487 g, 1 mmol), Meldrum's acid (1.3 equiv) and DMAP (2 equiv.) in 5 mL anhydrous dichloromethane was cooled in an ice-salt bath. To this reaction mixture, a solution of isopropenyl chloroformate (1.1 equiv) in 2 mL dichloromethane was added very slowly with vigorous stirring under nitrogen. The reaction mixture was allowed to stir in ice till the complete disappearance of the starting material was detected by TLC. Upon completion, 3 mL of a 10% aqueous solution of KHSO$_4$ was added to quench the reaction. The cooling bath was removed and another 3 mL of the KHSO$_4$ solution was added. After dilution with dichloromethane, the two phases were separated, and the organic fraction was washed twice with water, once with brine and dried over $Na_2SO_4$. Evaporation of the solvent gave the Meldrum's acid adduct; $R_f$ 0.5, petroleum ether:ethyl acetate (1:4), which was dissolved in benzene/methanol (4:1) and heated under reflux for 9 h. After evaporation of the solvent, the product can be further purified by column chromatography if desired to obtain 0.508 g (94%) compound 4 as colorless oil. $R_f$ 0.4 hexane/ethyl acetate (2:1). $^1$H NMR (CDCl$_3$, TMS, 400 MHz) δ 7.76 (d, J=7.2, 2H), 7.60 (d, J=7.2, 2H), 7.41 (t, J=7.2, 2H), 7.32 (t, J=7.2, 2H), 5.82 (d, J=8.8, 1H, NH), 4.81 (d, J=12, 1H), 4.77 (m, 1H), 4.73 (d, J=12, 1H), 4.42-4.46 (A part of an ABX system, $J_{AB}$=2.8, $J_{AX}$=7.6, 1H), 4.33-4.37 (B part of an ABX system, $J_{AB}$=2.8, $J_{BX}$=7.6, 1H), 4.23 (t, J=7.2, 1H), 3.74 (s, 3H), 3.51 (s, 2H), 3.39-3.45 (A part of an ABX system, $J_{AB}$=18.8, $J_{AX}$=4, 1H), 3.19-3.25 (B part of an ABX system, $J_{AB}$=18.8, $J_{BX}$=4, 1H). $^{13}$C NMR (CDCl$_3$, TMS, 90 MHz) δ 200.92, 169.50, 167.02, 156.28, 143.97, 143.86, 141.54, 128.01(×2), 127.35(×2), 125.35(×2), 120.26(×2), 94.52, 75.09, 67.69, 52.84, 49.91, 48.99, 47.28, 44.76. MS (MALDI/TOF) [$C_{24}H_{22}NO_7Cl_3$+Na]$^+$: Calculated: 564.04 (100%), 566.03 (96%). Found: 564 (87%), 566 (100%).

Example 4

Synthesis of 3-(7-hydroxy-2-oxo-2H-chromen-4-yl)-2-(9H-fluoren-9-yl-methoxycarbonylamino)-propionic acid 2,2,2-trichloro-ethyl ester (6)[14]

Resorcinol (5, 0.162 g, 1.47 mmol) was added to a solution of compound 4 (0.795 g, 1.47 mmol) in methanesulfonic acid in an ice bath. The resulting solution was allowed to stir at 0° C. for 6 h. After completion of the reaction, the mixture was poured into cold water and the precipitates were filtered to get an off white solid. Purification of the crude product by column chromatography, eluting with hexane:ethyl acetate (2:1) gave 6 as a white solid in 60% yield. $^1$H NMR (CDCl$_3$, TMS, 400 MHz) δ 8.86 (s, 1H), 7.76 (d, J=7.2, 2H), 7.63 (d, J=8.4, 1H), 7.55 (d, J=7.2, 2H), 7.40 (t, J=7.2, 2H), 7.30 (t, J=7.2, 2H), 6.88 (d, J=2.0, 1H), 6.86 (d, J=1.6, 1H), 6.16 (s, 1H), 5.97 (d, J=8.4, 1H), 4.84 (d, J=12, 1H), 4.83 (m, 1H), 4.74 (d, J=12, 1H), 4.39 (d, J=7.2, 2H), 4.19 (t, J=6.8, 1H), 3.40-3.45 (A part of an ABX system, $J_{AB}$=17.6, $J_{AX}$=5.2, 1H), 3.16-3.21 (B part of an ABX system, $J_{AB}$=17.6, $J_{BX}$=5.2, 1H). $^{13}$C NMR (CDCl$_3$, TMS, 100 MHz) δ 169.59, 161.76, 161.30, 156.08, 155.57, 151.21, 143.55, 141.28, 127.78(×2), 127.12(×2), 125.38 (×2), 125.02(×2), 120.01(×2), 113.73, 112.05, 111.38, 103.46, 94.13, 74.75, 67.28, 53.07, 46.97, 34.36. MS (MALDI/TOF) [$C_{29}H_{22}NO_7Cl_3$+Na]$^+$: Calculated: 624.04 (100%), 626.03 (96%). Found: 624 (100%), 626 (96%).

Example 5

Synthesis of 3-[7-(Diethoxyphosphoryloxy)-2-oxo-2H-chromen-4-yl]-2-(9H-fluoren-9-ylmethoxycarbonylamino)-propionic acid 2,2,2-trichloro-ethyl ester (7)[21]

To a solution of 6 (0.200 g, 0.33 mmol) in 15 mL anhydrous CHCl$_3$, DIPEA (0.107 g, 0.824 mmol) and diethyl chlorophosphate (0.078 g, 0.43 mmol) were added. The resulting mixture was allowed to stir at room temperature, under nitrogen for 14 h. Upon completion of the reaction (monitored by TLC), the reaction was quenched with a 5% KHSO$_4$ solution in water, washed with 5% KHSO$_4$, water, and 10% NaHCO$_3$, water, brine and dried over Na$_2$SO$_4$. Evaporation of the solvent gave the desired product as a white solid. Further purification by column chromatography over silica gel, eluting with 1:1 (Hexane:ethyl acetate) gave 0.194 g of 7 (80%) as a white solid. $^1$H NMR (CDCl$_3$, 400 MHz) δ 7.75 (d, J=7.6, 3H), 7.55 (d, J=7.6, 2H), 7.39 (t, J=7.6, 2H), 7.30 (t, J=7.6, 2H), 7.23 (m, 2H), 6.27 (s, 1H), 5.54 (d, J=7.2, 1H), 4.84 (d, J=12.4, 1H), 4.82 (m, 1H), 4.71 (d, J=12.4, 1H), 4.41 (d, J=6.8, 2H), 4.25 (m, 5H), 3.36-3.41 (A part of an ABX system, $J_{AB}$=14.8, $J_{AX}$=5.6, 1H), 3.15-3.20 (B part of an ABX system, $J_{AB}$=14.8, $J_{BX}$=5.6, 1H), 1.37 (t, J=6.8, 6H). $^{13}$C NMR (CDCl$_3$, TMS, 100 MHz) δ 169.26, 159.86, 155.77, 154.78, 153.47, 149.60, 143.43, 141.32, 127.86(×2), 127.14 (×2), 125.46 (×2), 124.99, 124.94, 120.08(×2), 116.91, 115.52, 109.11, 99.76, 93.98, 74.85, 67.46, 65.25, 65.08, 52.97, 46.98, 34.94, 16.08, 16.01. $^{31}$P NMR (CDCl$_3$, H$_3$PO$_4$, 162 MHz) δ −6.32. MS (MALDI/TOF) [$C_{33}H_{31}NO_{10}Cl_3$P+Na]$^+$: Calculated: 760.06 (100%), 762.06 (96%). Found: 760 (88%), 762 (100%).

Example 6

Synthesis of 3-[7-(Diethoxyphosphoryloxy)-2-oxo-2H-chromen-4-yl]-2-(9H-fluoren-9-ylmethoxycarbonylamino)-propionic acid (8)[19]

The trichloroethyl ester (0.274 g, 0.372 mmol) was dissolved in 20 mL THF/acetic acid (1:1), and allowed to stir at room temperature under nitrogen. Zinc dust (0.149 g, 2.23 mmol) was added to the reaction mixture and allowed to stir vigorously for 6 h or till the disappearance of the starting material. The reaction mixture was then filtered and the filtrate poured into water and extracted into diethyl ether. The combined extracts were washed with water, dried and the solvent evaporated to get the required product, which can be further purified using column chromatography on silica gel eluting with 3:7 (Hexane:ethyl acetate) to get 0.224 g of 8 (99%) as a white solid. $^1$H NMR (CDCl$_3$, TMS, 400 MHz) δ 7.81 (d, J=8.0, 1H), 7.74 (d, J=7.6, 2H), 7.55 (m, 2H), 7.37 (m, 2H), 7.30 (m, 2H), 7.18 (m, 2H), 6.27 (s, 1H), 5.76 (d, J=7.6, 1H), 4.68 (q, J=6.8, 1H), 4.38 (m, 2H), 4.24 (m, 5H), 3.26 (m, 2H), 1.37 (t, J=6.8, 6H). $^{13}$C NMR (CDCl$_3$, TMS, 100 MHz) δ 171.14, 161.32, 160.97, 155.80, 155.12, 143.56, 143.52, 141.30, 127.82(×2), 127.17(×2), 125.49(×2), 125.05, 125.00, 120.05(×2), 113.59, 112.27, 111.79, 103.70, 67.41, 53.35, 52.87, 47.01, 36.99, 36.97, 36.55, 35.16. $^{31}$P NMR (CDCl$_3$, H$_3$PO$_4$, 162 MHz) δ −7.35. MS (MALDI/TOF) [$C_{31}H_{30}NO_{10}$P+Na]$^+$: Calculated: 630.15. Found: 630. Elemental Analysis [$C_{31}H_{30}NO_{10}$P.H$_2$O] Calculated: C, 59.52; H, 5.16; N, 2.24. Found: C, 58.57; H, 5.34; N, 2.12.

B. Synthesis of Peptides Containing Phosphotyrosine, Tyrosine, or pCAP

Example 7

Synthesis of DADE-pY-GPAA-NH$_2$ (9a) and DADE-Y-GPAA-NH$_2$ (9b) where pY=phosphotyrosine, Y=tyrosine Peptides 9a and 9b were synthesized using standard solid phase amino acid coupling procedures.[15] Rink amide resin (100 mg, 7.4×10$^{-5}$ mol) was used as the solid support, and each new amino acid (5 equiv) was coupled to the growing chain using hydroxybenzotriazole (HOBt) and diisopropylcarbodiimide (DIPCDI) (5 equiv) in DMF as mediators. Each coupling reaction was run for 3 h. Removal of the N-terminal Fmoc group was accomplished by twice agitating the resin with 1 mL of 2% 1,8-diazabicyclo[5.4.0]undec-7-ene (DBU)

in DMF. The peptides were then cleaved from the resin under acidic conditions (1 mL of 95% trifluoroacetic acid, 2.5% $H_2O$, 2.5% triisopropylsilane) and purified twice on a C18 RP-HPLC column (Varian, Inc.). After characterization using MALDI-TOF spectrometry, stock solutions of each peptide were made by dissolving the peptides in DMSO. Peptide 9a and 9b were obtained in 48% and 33% yields, respectively. MS (MALDI/TOF) 9a, $C_{38}H_{55}N_{10}O_{19}P+H^+$ Calculated: 987.35, Found: 988. 9b, $C_{38}H_5N_{10}O_{16}+H^+$ Calculated: 907.38, Found: 907.

Example 8

Synthesis of DADE-pCAP-GPAA-$NH_2$ (10a) where pCAP=2-Amino-3-(2-oxo-7-phosphonooxy-2H-chromen-4-yl)-propionic acid Peptide 10a was synthesized in the same fashion as 9a and 9b above, with the exception that each amino acid was coupled to the growing peptide chain using Benzotriazol-1-yl-oxytripyrrolidinophosphonium hexafluorophosphate (Py-BOP) and HOBt as coupling agents. All amino acids were allowed to couple for 1 h. The phosphate protecting groups were removed by treating the resin with 20 equiv trimethylsilyliodide (TMSI) (0.1113 mL, 0.74 mmol) in anhydrous dichloromethane (1 mL). The beads were then washed with dichloromethane, followed by DMF. The N-terminal Fmoc group was then removed and the peptides cleaved off the resin as above. Following HPLC purification, the peptide 10a (20% yield) was characterized using MALDI-TOF spectrometry. MS (MALDI/TOF) 10a+$H^+$ Calculated: 1057.35, Found: 1054.

C. Assays

Example 9

Enzyme Activity Assay

Standard conditions employed to determine the kinetic constants of each substrate with YOP and TCPTP are described below. Substrates were dissolved in DMSO and diluted to the appropriate concentration in DMSO. Aliquots were taken such that each reaction had the same amount of DMSO, which never exceeded 5% of the reaction volume (usually 200 μL). The buffer used for all studies contained 50 mM HEPES, pH 7.1, 100 mM NaCl, 2 mM EDTA, 0.01% Brij 35, 1 mM dithiothreitol (DTT). Prior to each reaction, the enzyme was incubated in buffer with freshly added DTT for 10 min on ice. In each reaction, the concentration of enzyme was fixed at between 1 and 2 nM and the substrate concentration varied from 0 to 2.5 mM. The YOP reactions were run at room temperature, but the TCPTP reactions were done at 30° C. The increase in signal (absorbance or fluorescence) due to substrate hydrolysis was measured every 60 s for 30 min. Each reaction was run in triplicate and the results averaged. Standard curves were prepared using authentic samples of the appropriate product, relative fluorescence or absorbance units were converted into concentration of product formed, and the resulting data was fit to the Michaelis-Menten equation, providing kinetic parameters for each substrate.

Results of the assay are present in FIGS. 2-5.

Example 10

Enzyme Profile Assay

Figure 6:
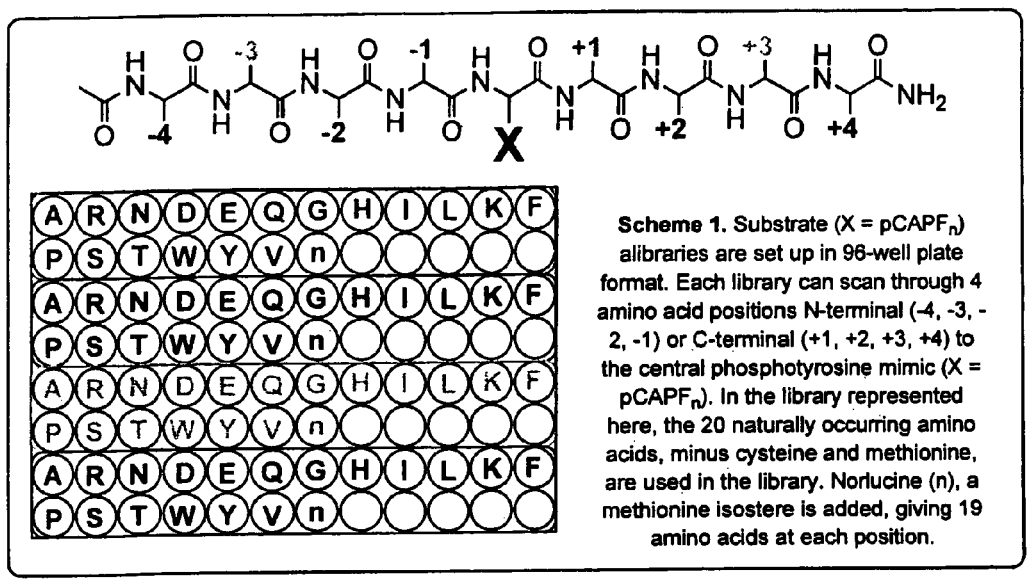
FIG. 6. Schematics representing a peptide substrate library of the present invention FIG. 7. Characteristics profiles of 5 different enzymes FIG. 8. Mu kinetics with Csk
Figure 7:
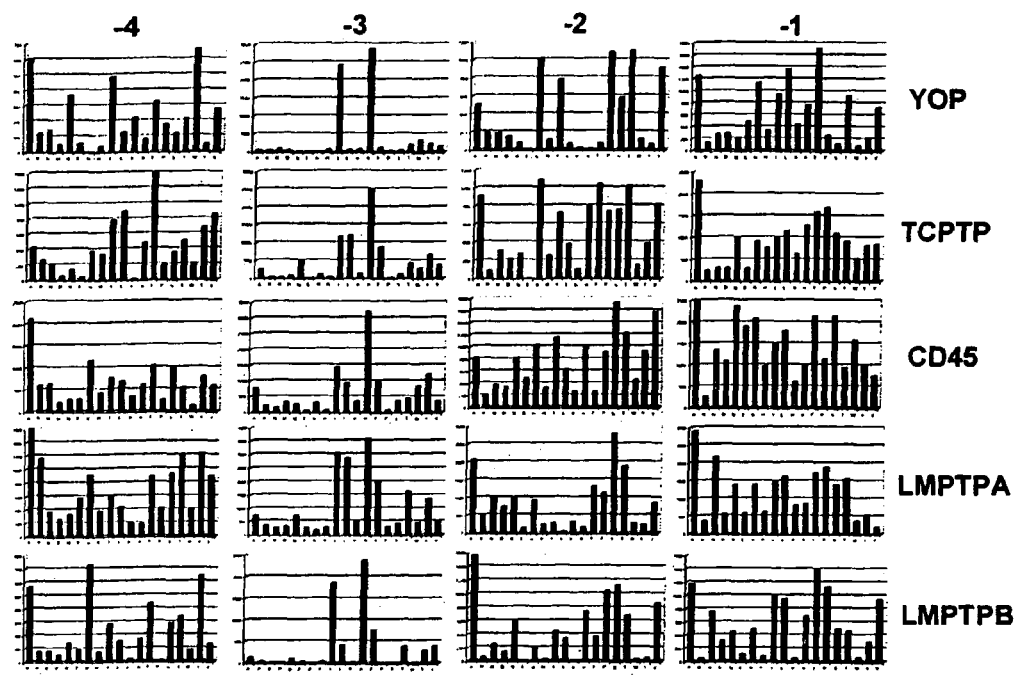

We have developed two combinatorial peptide substrate libraries in which the amino acid sequence on either the N-terminal or the C-terminal side of the pCAP moiety is varied. All possible peptide sequences are contained in these two libraries, as outlined in Scheme 1 shown in FIG. 6. These libraries are designed to provide information about the amino acid(s) most preferred by a given enzyme at each position in the peptide chain. These libraries can be used to determine the optimal peptide substrate for any given PTP. These libraries can also be used to aid in the design of potent, selective PTP inhibitors. When assaying substrate specificity with the pCAP-based substrate libraries, a large increase in fluorescence in a given well indicates that the amino acid in that well is favored.

Figure 2:
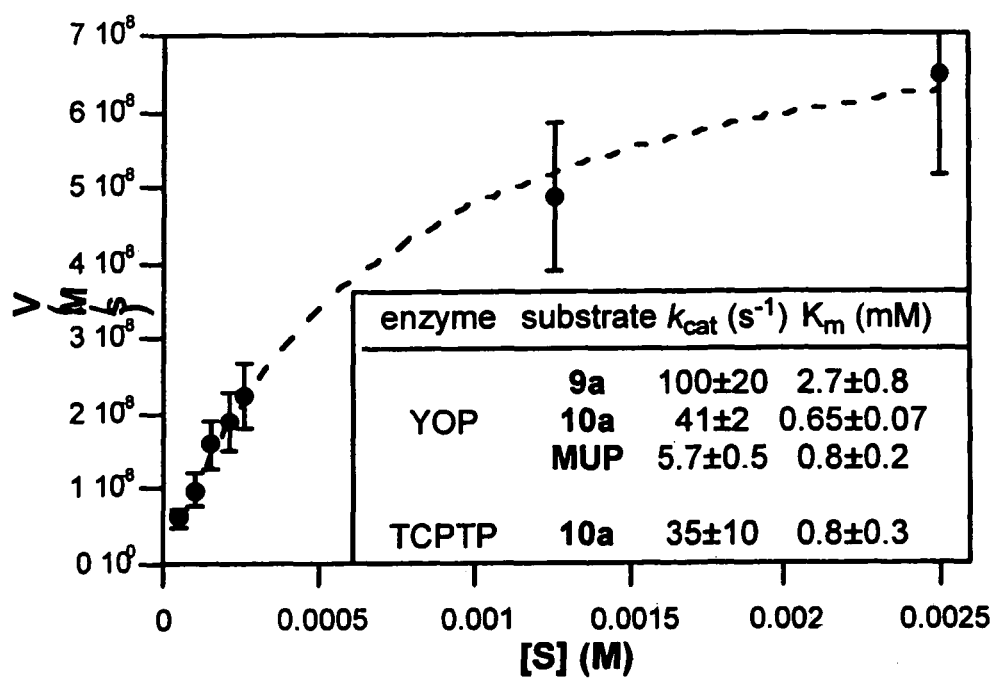
FIG. 2. Hydrolysis of 10a by YOP. Inlaid data shows a comparison of the kinetic parameters of PTP-catalyzed hydrolysis of 9a, 10a, and MUP.
Figure 3:
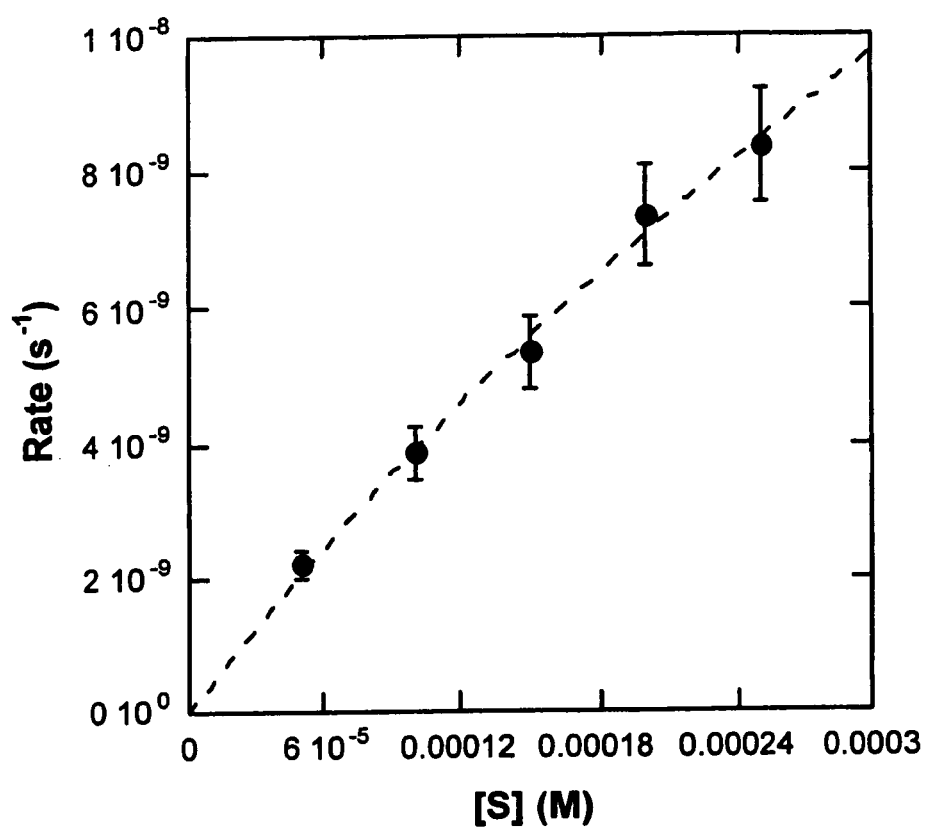
FIG. 3. Hydrolysis of 10a by TCPTP. The dashed line represents the best fit of the data to the Michaelis-Menten equation with $k_{cat}=35\pm10$ s$^{-1}$ and $K_m=0.8\pm0.3$ mM.
Figure 4:
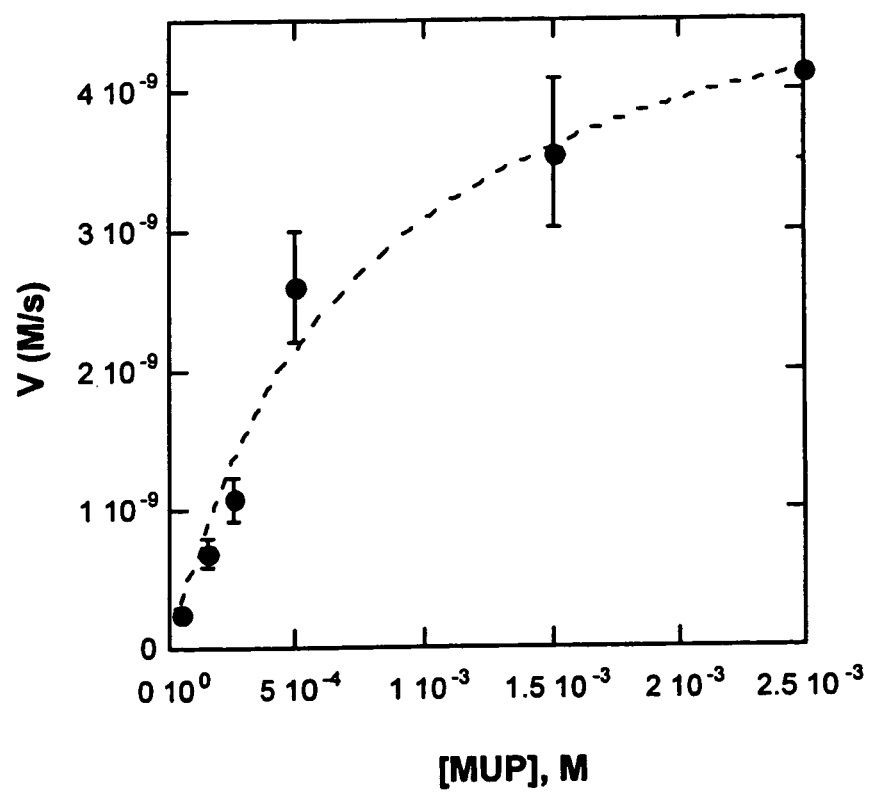
FIG. 4. Hydrolysis of MUP by YOP. The dashed line represents the best fit of the data to the Michaelis-Menten equation with $k_{cat}=5.7\pm0.5$ s$^{-1}$ and $K_m=0.8\pm0.2$ mM.
Figure 5:
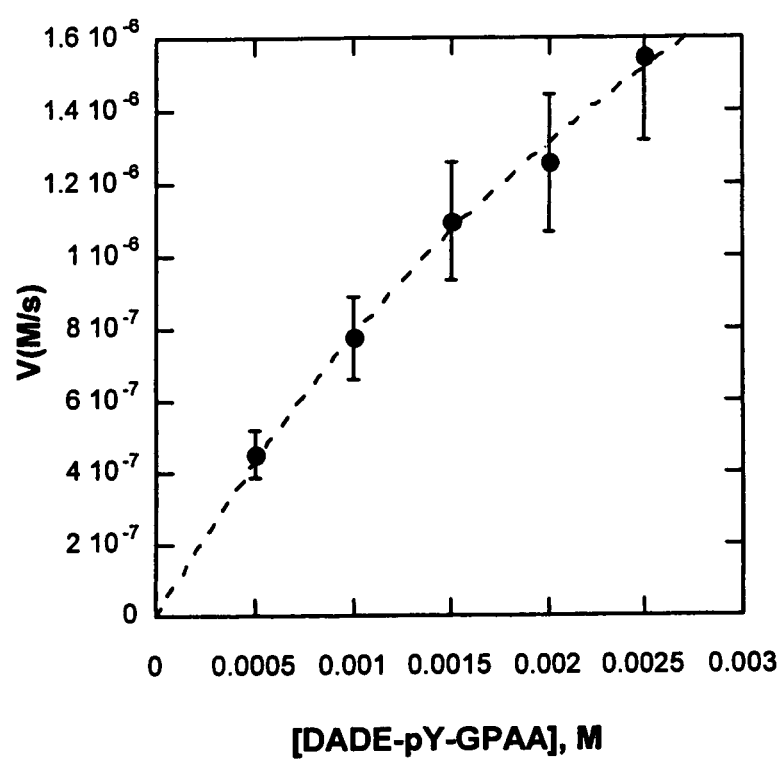
FIG. 5. Hydrolysis of 9a by YOP. The dashed line represents the best fit of the data to the Michaelis-Menten equation with $k_{cat}=100\pm20$ s$^{-1}$ and $K_m=2.7\pm0.8$ mM.

As a proof of principle, we have synthesized a library where the N-terminal amino acid positions are varied and the amino acids C-terminal to the pCAP residue are fixed as the sequence Leu-Ala-Ala (N-terminal library) and a second library where the N-terminal amino acids are fixed as the sequence Asp-Ile-Asp-Glu and the amino acids C-terminal to the pCAP residue are varied (C-terminal library). We have tested these libraries with several different PTP enzymes. Representative N-terminal library profile data for five different PTP enzymes is shown in FIG. 2. Although the enzymes display similar substrate specificity profiles, there are some key differences between enzymes. For example, at the −1 position, CD45 is the only enzyme with high turnover rates for glutamine and glutamate. In the −4 position, only LMPTPA shows a high turnover of substrates containing arginine. Differences such as these can be exploited in the development of potent, selective PTP inhibitors.

Example 11

Kinase Assay

Figure 8:
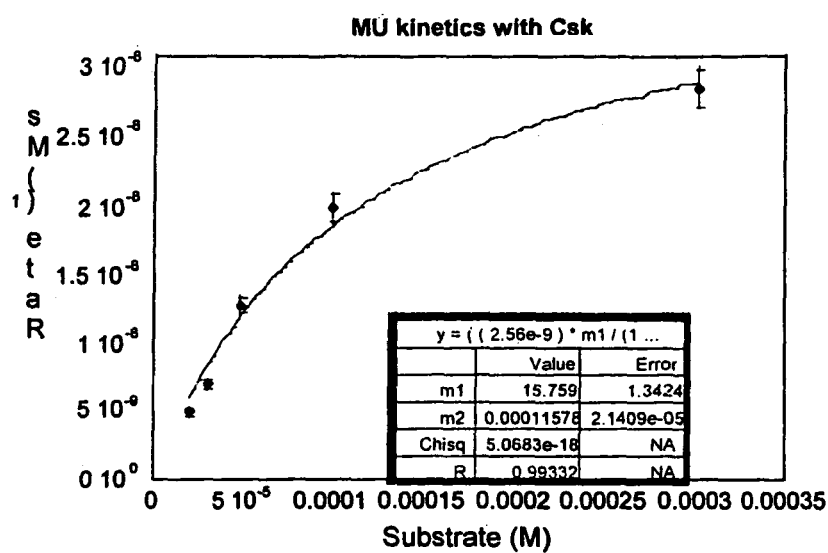

Currently kinases assays are done using radioactive ATP. We envision that a highly sensitive fluorescence based assay would be more convenient. MU, an analog of CAP, was tested as a substrate for the protein tyrosine kinase Csk, to check the viability of the idea (FIG. 8). We observed that Csk indeed phosphorylated MU to MUP. In addition, the fluorinated derivatives also serve as sensitive fluorescent assays for PTK activity.

Experimental

Stock solutions of MU were prepared in DMSO to make 1 and 10 mM solutions. For enzymatic assays, various aliquots of each substrate and DMSO (to a total of 5 μL) were placed on a 96 well plate, incubated with 75 μL buffer (30 mM HEPES, 5 mM $MgCl_2$, 0.01% Brij 35, pH 6.8) for 5 mins, treated with 1 μL of 10 mM ATP, followed by 20 μL of 12.8 nM Csk. The decrease in signal (fluorescence) due to substrate phosphorylation was measured every 60 s for 30 min. Each reaction was run in triplicate and the results averaged. Standard curves were prepared using authentic samples of the appropriate substrate, relative fluorescence units were converted into concentration of substrate left unreacted, and the resulting data was fit to the Michaelis-Menten equation, providing kinetic parameters for each substrate.

While the present invention has been described herein with specific details by way of illustrations and examples and with reference to certain preferred embodiments thereof, those of ordinary skill in the art will readily recognize that numerous modifications, substitutions, and alterations are possible without departing from the spirit and scope of the invention. It is intended that all of these modifications and variations be within the scope of the present invention as described and claimed herein, and that the invention be limited only by the scope of the claims which follow, and that such claims be interpreted as broadly as reasonable.

What is claimed is:

1. A coumarin-based compound having the formula:

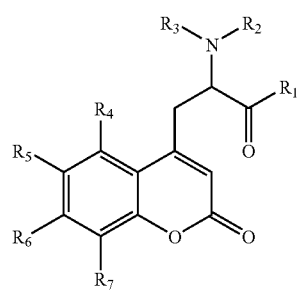

wherein,
$R_1$ is a peptide;
$R_2$ is a peptide;
$R_3$ is a H;
$R_4$ is a H;
$R_5$ is a H;
$R_6$ is $OPO_3H_2$;
$R_7$ is a H;
wherein,
$R_1$ and $R_2$ form a ring structure.

2. A composition comprising a compound having the formula:

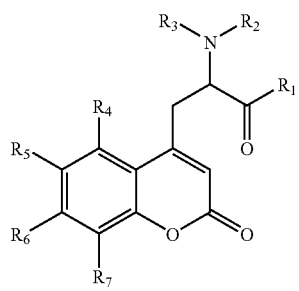

wherein,
$R_1$ is a peptide;
$R_2$ is a peptide;

23

R₃ is a H;
R₄ is a H;
R₅ is a H;
R₆ is OPO₃H₂;
R₇ is a H;
wherein,
R₁ and R₂ form a ring structure; or
a salt thereof.

3. The compound of claim 1, wherein
R₁ is the peptide DADE;
R₂ is the peptide LIPQQG.

4. An assay kit for assaying an enzyme comprising a compound having the formula:

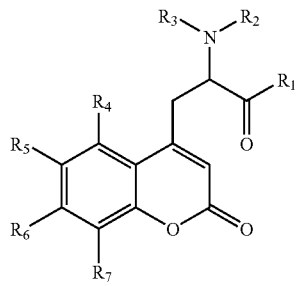

wherein,
R₁ is a peptide;
R₂ is a peptide;
R₃ is a H;
R₄ is a H;
R₅ is a H;
R₆ is OPO₃H₂;
R₇ is a H;
wherein,
R₁ and R₂ form a ring structure.

5. The kit of claim 4 wherein said enzyme is one selected from the group consisting of phosphatase, kinase, amidase, peptidase, protease, glycosidase, and sulfatase.

6. A biosensor, comprising:
a sensing element comprising at least one target fluorescent coumaryl peptide having the formula:

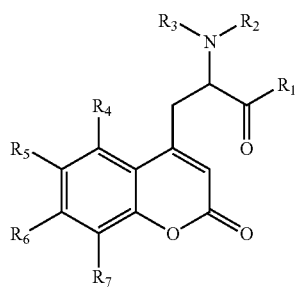

wherein,
R₁ is a peptide;
R₂ is a peptide;
R₃ is a H;
R₄ is a H;
R₅ is a H;
R₆ is OPO₃H₂;
R₇ is a H;

24 wherein,
R₁ and R₂ form a ring structure,
and wherein a change in a fluorescence intensity of the target peptide indicates that the target peptide is recognized by the enzyme.

7. A coumaryl compound having the formula:

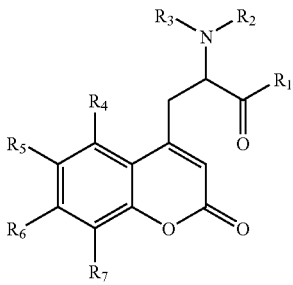

wherein,
R₁ is a peptide;
R₂ is a peptide;
R₃ is a H;
R₄ is a H;
R₅ is a H or F;
R₇ is a H or F;
wherein R₁ and R₂ form a sequence that is recognized by a kinase or a phosphatase;
and wherein R₆ is one selected from the group consisting of aminophosphate, phosphoramidate, OPO₃H₂, OPO₃²⁻, OPO₃R₈R₉, and wherein R₈ and R₉ are independently selected from a group consisting of H, halogen alkyl, aryl, ether, ester, nitrile, azide, thiol, thioester, OH, sulfate, phosphate, sulfonate, phosphonate, primary amine, secondary amine, tertiary amine, primary amide, secondary amide, carboxyl, and carbamoyl functional group.

8. A peptide of about 2 to 100 residues, wherein said peptide is a kinase or a phosphatase substrate comprising at least one coumaryl alpha-amino acid residue having a sidechain according to the following formula:

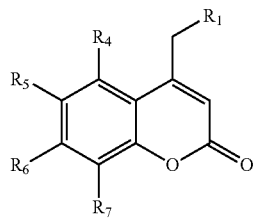

wherein,
R₁ is the alpha carbon of the coumaryl amino acid residue;
R₄ is a H;
R₅ is a H or F;
R₇ is a H or F;
and wherein R₆ is one selected from the group consisting of aminophosphate, phosphoramidate, OPO₃H₂, OPO₃²⁻, OPO₃R₈R₉, and wherein R₈ and R₉ are independently selected from a group consisting of H, halogen alkyl, aryl, ether, ester, nitrile, azide, thiol, thioester, OH, sulfate, phosphate, sulfonate, phosphonate, primary amine, secondary amine, tertiary amine, primary amide, secondary amide, carboxyl, and carbamoyl functional group.

9. The coumaryl compound of claim 7, wherein said sequence formed by $R_1$ and $R_2$ is recognized by both a phosphatase and a kinase.

10. The coumaryl compound of claim 9, wherein said phosphatase is a protein tyrosine phosphatase and said kinase is a protein tyrosine kinase.

11. The peptide of claim 8 wherein said peptide is a substrate of both a kinase and a phosphatase.

12. The peptide of claim 11 wherein said kinase is a protein tyrosine kinase and said phosphatase is a protein tyrosine phosphatase.

* * * * *

SEQUENCE LISTING

```
<160> NUMBER OF SEQ ID NOS: 3

<210> SEQ ID NO 1
<211> LENGTH: 11
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (5)..(7)
<223> OTHER INFORMATION: "Xaa" is  phosphotyrosine

<400> SEQUENCE: 1

Asp Ala Asp Glu Xaa Ala Ala Gly Pro Ala Ala
1               5                   10

<210> SEQ ID NO 2
<211> LENGTH: 9
<212> TYPE: PRT
<213> ORGANISM: Artificial
<220> FEATURE:
<223> OTHER INFORMATION: Synthetic

<400> SEQUENCE: 2

Asp Ala Asp Glu Tyr Gly Pro Ala Ala
1               5

<210> SEQ ID NO 3
<211> LENGTH: 11
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (5)..(7)
<223> OTHER INFORMATION: "Xaa" is
      2-Amino-3-(2-oxo-7-phosphonooxy-2H-chromen-4-yl)-propionic acid

<400> SEQUENCE: 3

Asp Ala Asp Glu Xaa Ala Ala Gly Pro Ala Ala
1               5                   10
```